(12) United States Patent
Roberts et al.

(10) Patent No.: US 10,471,220 B2
(45) Date of Patent: *Nov. 12, 2019

(54) SAFETY DEVICE FOR A PRE-FILLED SYRINGE AND AN INJECTION DEVICE

(71) Applicant: Sanofi-Aventis Deutschland GMBH, Frankfurt am Main (DE)

(72) Inventors: Gareth Roberts, Frankfurt am Main (DE); Matthew Ekman, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 244 days.

This patent is subject to a terminal disclaimer.

(21) Appl. No.: 15/419,295

(22) Filed: Jan. 30, 2017

(65) Prior Publication Data

US 2017/0143911 A1 May 25, 2017

Related U.S. Application Data

(63) Continuation of application No. 13/976,418, filed as application No. PCT/EP2011/074275 on Dec. 30, 2011, now Pat. No. 9,592,350.

(30) Foreign Application Priority Data

Jan. 4, 2011 (EP) .................................... 11150077

(51) Int. Cl.
  *A61M 5/32* (2006.01)
(52) U.S. Cl.
  CPC ........ *A61M 5/3234* (2013.01); *A61M 5/3202* (2013.01); *A61M 5/326* (2013.01);
  (Continued)

(58) Field of Classification Search
  CPC .............. A61M 5/3202; A61M 5/3232; A61M 5/3234; A61M 5/3257; A61M 5/326
  See application file for complete search history.

(56) References Cited

U.S. PATENT DOCUMENTS 9,592,350 B2 * 3/2017 Roberts ............... A61M 5/3234
2009/0270804 A1 10/2009 Mesa et al.
(Continued)

FOREIGN PATENT DOCUMENTS

FR  2905273     3/2008
RU  2 203 688    7/2002
(Continued)

OTHER PUBLICATIONS

International Preliminary Report on Patentability in international Application No. PCT/EP2011/074275, dated Jul. 10, 2013, 5 pages.
(Continued)

*Primary Examiner* — Laura A Bouchelle
(74) *Attorney, Agent, or Firm* — Fish & Richardson P.C.

(57) ABSTRACT

A safety device for a pre-filled syringe is proposed that comprises
  a hollow support body with a helical groove formed into an inner surface thereof,
  a mounting collar for mounting the pre-filled syringe to the support body,
  a spinning collar with a helical tongue formed to an outer surface thereof and
  a torsion spring.
The helical groove accommodates the helical tongue. Upon release, the torsion spring is capable of exerting a torque upon the spinning collar which causes the spinning collar to rotate within the support body. The engagement of the helical groove and the helical tongue redirects the rotational
(Continued)

movement of the spinning collar to a translatory movement that moves the mounting collar in a proximal direction.

14 Claims, 8 Drawing Sheets

Specification includes a Sequence Listing.

(52) U.S. Cl.
CPC ........ *A61M 5/3243* (2013.01); *A61M 5/3257* (2013.01); *A61M 2005/3241* (2013.01); *A61M 2005/3267* (2013.01)

(56) References Cited

U.S. PATENT DOCUMENTS

2010/0280460 A1* 11/2010 Markussen ......... A61M 5/2033
604/195
2013/0331795 A1   12/2013 Roberts et al.

FOREIGN PATENT DOCUMENTS

| WO | WO 2004/047892 | 6/2004 |
| WO | WO 2005/115509 | 12/2005 |

OTHER PUBLICATIONS

International Search Report and Written Opinion in International Application No. PCT/EP2011/074275, dated Feb. 14, 2012, 6 pages.

\* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
        35
```

SAFETY DEVICE FOR A PRE-FILLED SYRINGE AND AN INJECTION DEVICE

CROSS REFERENCE TO RELATED APPLICATIONS

The present application is a continuation of U.S. patent application Ser. No. 13/976,418, filed Jun. 26, 2013, which is a U.S. National Phase Application pursuant to 35 U.S.C. § 371 of International Application No. PCT/EP2011/074275, filed Dec. 30, 2011, which claims priority to European Patent Application No. 11150077.3, filed Jan. 4, 2011. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shroud that is either manually moved or moved by the action of a relaxing spring to surround the needle.

A different type of safety device known in the state of the art achieves the object of providing needle safety by arranging the pre-filled syringe movable relative to a body, where the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a hollow support body with a helical groove formed into an inner surface thereof,
a mounting collar for mounting the pre-filled syringe to the support body,
a spinning collar with a helical tongue formed to an outer surface thereof and
a torsion spring.

The helical groove accommodates the helical tongue. Upon release, the torsion spring is capable of exerting a torque upon the spinning collar which causes the spinning collar to rotate within the support body. The engagement of the helical groove and the helical tongue redirects the rotational movement of the spinning collar to a translatory movement that moves the mounting collar in a proximal direction.

The safety device provides needle safety for an injection needle attached to a distal end of the pre-filled syringe after an injection is completed. The pre-filled syringe may be attached to the mounting collar, so that the proximal movement of the mounting collar safely retracts the pre-filled syringe to a retracted position. In the retracted position, the used injection needle is surrounded by the support body to prevent accidental needle stick injuries. In particular, infections resulting from needle stick injuries with contaminated injection needles are thus avoided.

The torsion spring is arranged within the support body in a pre-tensioned state. The torsion spring provides a reliable energy source for the retraction mechanism providing needle safety after the injection is completed. Upon the release of the mounting collar, the torsion spring exerts a torque upon the spinning collar which in turn starts to rotate within the support body.

The spinning collar may comprise a bearing surface that bears against the mounting collar in the proximal direction, so that the spinning collar may push the mounting collar and the pre-filled syringe attached thereto in the proximal direction. The bearing surface is essentially ring-shaped, so that an area that abuts the mounting collar is reduced. This helps to reduce unintentional friction between the mounting collar and the spinning collar. As the spinning collar rotates around a central axis of the safety device while the mounting collar and the pre-filled syringe attached thereto are retracted, occurring high friction between the mounting collar and the spinning collar may cause one of these parts to get stuck within the support body and/or a failure of the retraction mechanism of the safety device. The bearing surface of reduced area thus ensures a reliable use of the safety device.

According to a possible embodiment of the invention, the mounting collar is releasably mounted to the support body by a catch protruding through an aperture formed into the support body. The mounting collar is thus releasably mounted to the support body by particularly simple means that efficiently prevent an early release of the mounting collar.

An outer body may be slidably arranged with respect to the support body, wherein the outer body substantially receives the support body at the end of an injection stroke delivering a dose of medication beneath the skin of a patient. The catch protruding through the aperture of the support body is inwardly deflected by the outer body to release the mounting collar at the end of the injection stroke. A further interaction of the user performing the injection is not necessary to release the mounting collar. The mounting collar is automatically released upon completion of the injection stroke.

According to another possible embodiment of the invention, the catch latches to a distal end of the support body to lock the mounting collar in the retracted position. The injection needle is surrounded and protected by the support body in the retracted position to avoid needle stick injuries. The catch locks the mounting collar and the pre-filled syringe comprising the injection needle in the retracted position and thus prevents a re-exposure of the injection needle.

According to yet another possible embodiment of the invention, a needle shroud is slidably arranged with respect to the support body. A first flange adapted to be pressed against a skin surface is formed to a distal end of the needle shroud. During the injection, the first flange rests on the skin surface. The needle shroud may be made from an opaque plastics material to hide the injection needle from the view of a patient throughout the injection. This may help to ease a possible fear of needles of the patient.

Alternatively, the needle shroud may be made from a transparent plastics material that allows the user to visually confirm the correct placement of the injection needle. This alternative embodiment is thus particularly suited for intra-vascular injections.

According to yet another possible embodiment of the invention, a second flange adapted to be pressed against skin surface is formed to a distal end of the support body. A needle shroud is omitted. Thus, the safety device of this embodiment only comprises a few parts preferably made from a plastics material. The safety device may thus be mass-produced at low costs.

According to the invention, an injection device comprises a safety device and a pre-filled syringe. An injection needle is attached to a distal end of the pre-filled syringe. The safety device comprises
  a hollow support body with a helical groove formed into an inner surface thereof,
  a mounting collar for mounting the pre-filled syringe to the support body,
  a spinning collar with a helical tongue formed to an outer surface thereof and
  a torsion spring.

The helical groove accommodates the helical tongue. Upon release, the torsion spring is capable of exerting a torque upon the spinning collar which causes the spinning collar to rotate within the support body. The engagement of the helical groove and the helical tongue redirects the rotational movement of the spinning collar to a translatory movement that moves the mounting collar and the pre-filled syringe in the proximal direction to a retracted position. In the retracted position, the injection needle is surrounded by the support body. The injection device comprising the pre-filled syringe and the safety device combines the aforementioned advantages and avoids inadvertent needle sticks injuries. The injection device is cheap to manufacture and is disposed after a single injection has been carried out.

The outer body may abut a plunger of the pre-filled syringe. Alternatively, the outer body may be attached to the plunger. A distal movement of the outer body with respect to the support body causes the plunger to depress into an inner cavity containing a dose of medication, whereby the dose of medication is expelled through the injection needle. The outer body may be gripped by the user and is manually pushed towards the skin of the patient in a single linear stroke to inject the dose of medication. The injection is carried out in a simple manner and may thus be safely performed even by inexperienced users.

The injection device is suited for self-administered injections and for injections administered by a health care professional. Consequently, the person referred to as the user or the patient may be one and the same person. Furthermore, the injection device may be used for intramuscular, subcutaneous or intravascular injections.

The pre-filled syringe may be filled with a medicament.

The term "medication", or "drug", or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
  H-(Lys)4-des Pro36, des Pro37 Exendin-4(1-39)-NH2,
  H-(Lys)5-des Pro36, des Pro37 Exendin-4(1-39)-NH2,
  des Pro36 Exendin-4(1-39),
  des Pro36 [Asp28] Exendin-4(1-39),
  des Pro36 [IsoAsp28] Exendin-4(1-39),
  des Pro36 [Met(0)14, Asp28] Exendin-4(1-39),
  des Pro36 [Met(0)14, IsoAsp28] Exendin-4(1-39),
  des Pro36 [Trp(02)25, Asp28] Exendin-4(1-39), des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
H-(Lys)6-des Pro36 [Met(0)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(0)14, Asp28] Exendin-4(1-39)-NH2,
H-Asn-(Glu)5-des Pro36, Pro37, Pro38 [Met(0)14, Asp28] Exendin-4(1-39)-NH2,
des Pro36, Pro37, Pro38 [Met(0)14, Asp28] Exendin-4(1-39)-(Lys)6-NH2,
H-(Lys)6-des Pro36, Pro37, Pro38 [Met(0)14, Asp28] Exendin-4(1-39)-(Lys)6-NH2,
H-Asn-(Glu)5 des Pro36, Pro37, Pro38 [Met(0)14, Asp28] Exendin-4(1-39)-(Lys)6-NH2,
H-Lys6-des Pro36 [Met(0)14, Trp(02)25, Asp28] Exendin-4(1-39)-Lys6-NH2,
H-des Asp28 Pro36, Pro37, Pro38 [Met(0)14, Trp(02)25] Exendin-4(1-39)-NH2,
H-(Lys)6-des Pro36, Pro37, Pro38 [Met(0)14, Asp28] Exendin-4(1-39)-NH2,
H-Asn-(Glu)5-des Pro36, Pro37, Pro38 [Met(0)14, Trp(02)25, Asp28] Exendin-4(1-39)-NH2,
des Pro36, Pro37, Pro38 [Met(0)14, Trp(02)25, Asp28] Exendin-4(1-39)-(Lys)6-NH2,
H-(Lys)6-des Pro36, Pro37, Pro38 [Met(0)14, Trp(02)25, Asp28] Exendin-4(S1-39)-(Lys)6-NH2,
H-Asn-(Glu)5-des Pro36, Pro37, Pro38 [Met(0)14, Trp(02)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
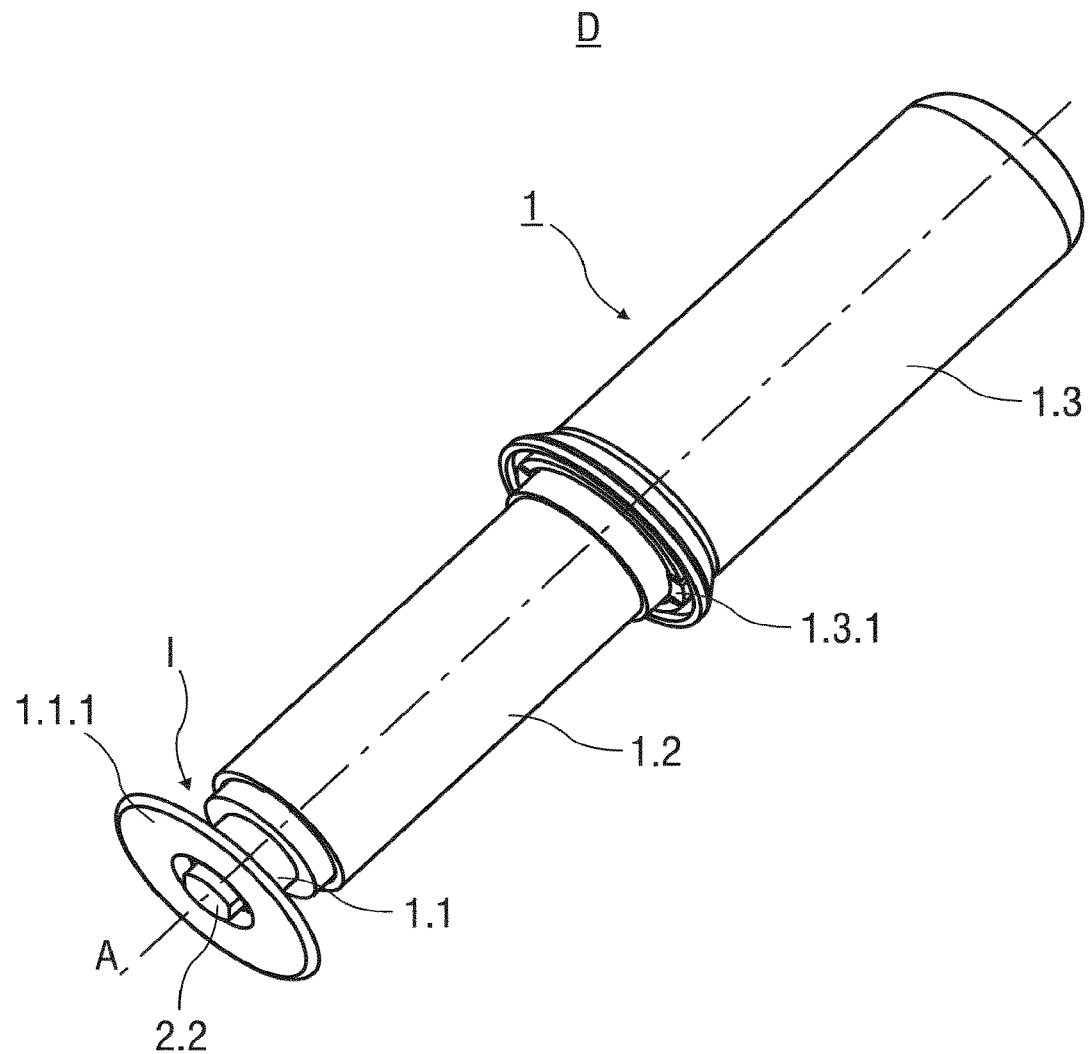
FIG. 1 shows a perspective view of an injection device according to a first embodiment of the invention prior to use comprising a safety device and a pre-filled syringe.

FIG. 1 shows an injection device D with a safety device 1 for a pre-filled syringe 2 according to a first embodiment of the invention as it would be presented to a user performing an injection. The safety device 1 comprises a substantially cylindrical and hollow needle shroud 1.1. The needle shroud 1.1 is received within a substantially cylindrical and hollow support body 1.2, wherein the needle shroud 1.1 is slidable with respect to the support body 1.2. Before usage of the safety device 1, the needle shroud 1.1 is retained in an initial first position I, wherein the needle shroud 1.1 protrudes the support body 1.2 in a distal direction.

Alternatively, the needle shroud 1.1 comprises a radial diameter that is sized to substantially receive the support body 1.2. In this alternative embodiment the support body 1.2 slides into the needle shroud 1.1 when the needle shroud 1.1 is moved from the first position I to a retracted second position II.

FIG. 1 shows the safety device 1 that comprises an essentially cylindrical and hollow outer body 1.3 with an open distal and a closed proximal end. The proximal end of the support body 1.2 is received within the open distal end of the outer body 1.3, whereas the outer body 1.3 is slidable with respect to the support body 1.2 in a distal direction to substantially receive the support body 1.2.

A circumferential and outwardly protruding support flange 1.3.1 is integrally formed to an outer surface of the outer body 1.3 close to its distal end. The outer body 1.3 may be gripped and pushed by a user in the distal direction, whereby the support flange 1.3.1 supports the hand of the user performing the injection stroke.

Preferably, the needle shroud 1.1, the support body 1.2 and the outer body 1.3 are made from a plastics material.

The needle shroud 1.1 comprises a circumferential first flange 1.1.1 at its distal end. The first flange 1.1.1 is adapted to be pressed against the skin of a patient and protrudes radial outwardly and perpendicularly to a central axis A of the safety device 1. Edges of the first flange 1.1.1 that may touch the skin of the patient are rounded to avoid injuries. The first flange 1.1.1 has a central opening centred on the central axis A of the safety device 1. The first flange 1.1.1 is integral to the needle shroud 1.1 or alternatively a separate part attached to the needle shroud 1.1 that is made from a plastics material.

Figure 2:
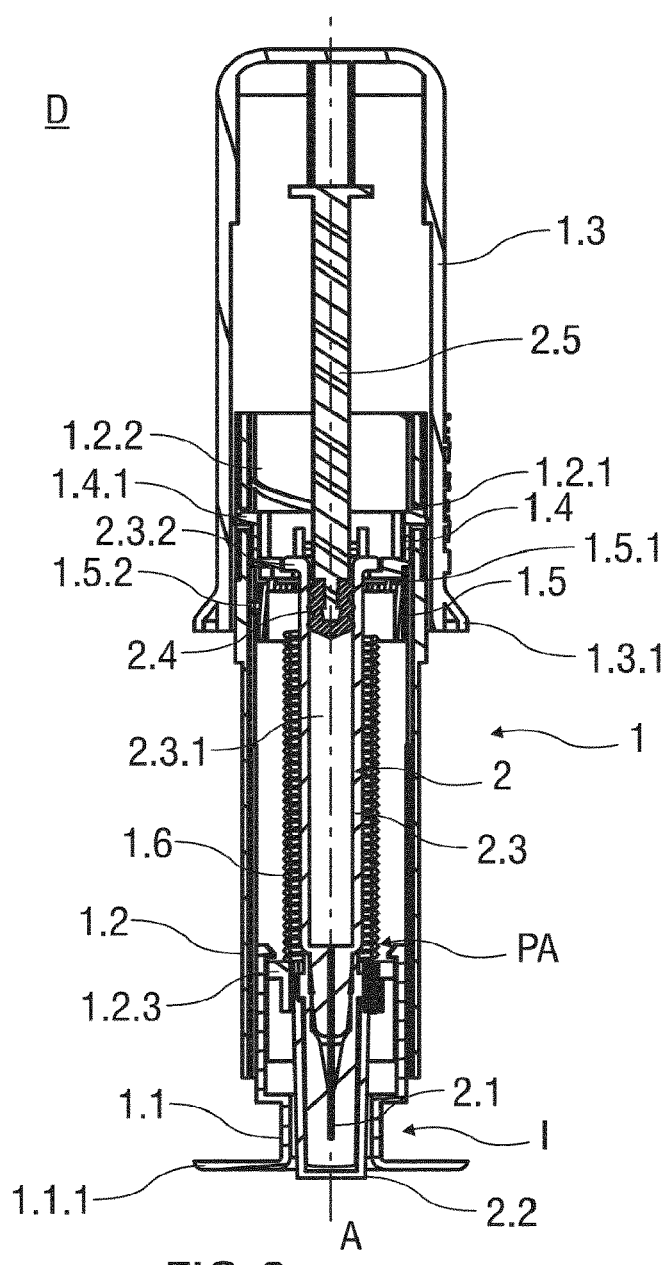
FIG. 2 shows a sectional view of an injection device according to the first embodiment of the invention prior to use.

In the packaged state shown in FIGS. 1 and 2, an injection needle 2.1 of the pre-filled syringe 2 is covered by a needle cap 2.2. Preferably, the needle cap 2.2 is at least partially made from a plastics material like rubber. The needle cap 2.2 protrudes the first flange 1.1.1 in the distal direction, so that the user can easily remove the needle cap 2.2 before an injection is performed.

FIG. 2 shows a perspective view of the injection device D as it would be delivered to a user. The injection device D comprises the safety device 1 and the pre-filled syringe 2 that is received in the support body 1.2. The pre-filled syringe 2 comprises the injection needle 2.1 covered by a needle cap 2.2 frictionally affixed to a distal end of a barrel 2.3. The barrel 2.3 has an inner cavity 2.3.1 containing a dose of medication. The inner cavity 2.3.1 is in fluid communication with the injection needle 2.1. A proximal end of the inner cavity 2.3.1 is fluid-tightly sealed by a stopper 2.4 that is connected to a plunger 2.5. The stopper 2.4 is movable in at least the distal direction by pushing the plunger 2.5 protruding the barrel 2.3 in the proximal direction.

The barrel 2.3 of the pre-filled syringe 2 comprises a barrel collar 2.3.2 that is attached to a mounting collar 1.4 mounting the pre-filled syringe 2 within the support body 1.2. A catch 1.4.1 formed to the mounting collar 1.4 releasably mounts the mounting collar 1.4 to the support body 1.2. The catch 1.4.1 protrudes through an aperture 1.2.1 formed into the support body 1.2 to mount the mounting collar 1.4 and the pre-filled syringe 2 attached thereto in an advanced position PA, wherein the injection needle 2.1 protrudes the support body 1.2 in the distal direction.

Upon release, the mounting collar 1.4 may travel proximally with respect to the support body 1.2 in a linear translatory motion. A linear guide rail or channel is formed to an inner surface of the support body 1.2 that engages the mounting collar 1.4 to prevent a rotation, so that the mounting collar 1.4 is forced to move in a linear motion with respect to the support body 1.2.

A spinning collar 1.5 comprises a proximal bearing surface 1.5.1 that bears against the mounting collar 1.4 in the proximal direction. The spinning collar 1.5 is biased by a torsion spring 1.6 arranged within the support body 1.2. The torsion spring 1.6 is in a pre-tensioned state and thus capable of exerting a torque upon the spinning collar 1.5 to make the spinning collar 1.5 rotate around the central axis A of the injection device D.

The spinning collar 1.5 comprises a helical tongue 1.5.2 that is accommodated in a helical groove 1.2.2 formed to an inner surface of the support body 1.2. The engagement of the helical tongue 1.5.2 and the helical groove 1.2.2 redirects a rotational movement of the spinning collar 1.5 into a translatory motion, so that the released mounting collar 1.4 may be pushed proximally by the rotating spinning collar 1.5.

The torsion spring 1.6 bears against an inner bearing surface 1.2.3 of the support body 1.2 in the distal direction and against the spinning collar 1.5 in the proximal direction.

The plunger 2.5 abuts an inner surface of the outer body 1.3, so that the plunger 2.5 may be depressed into the inner cavity 2.3.1 of the barrel 2.3 by manually pushing the outer body 1.3 in the distal direction.

Figure 3:
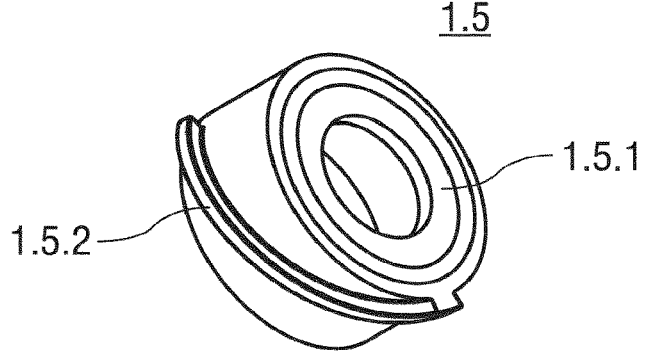
FIG. 3 shows a perspective view of a spinning collar.

FIG. 3 shows the spinning collar 1.5 with the helical tongue 1.5.2 formed to the outer surface thereof in a perspective view. The bearing surface 1.5.1 of the spinning collar 1.5 is essentially ring-shaped and reduces the area of the spinning collar 1.5 that abuts the mounting collar 1.4. Thus, occurring friction between a rotating spinning collar 1.5 and the rotationally fixed mounting collar 1.4 is reduced.

Figure 4A:
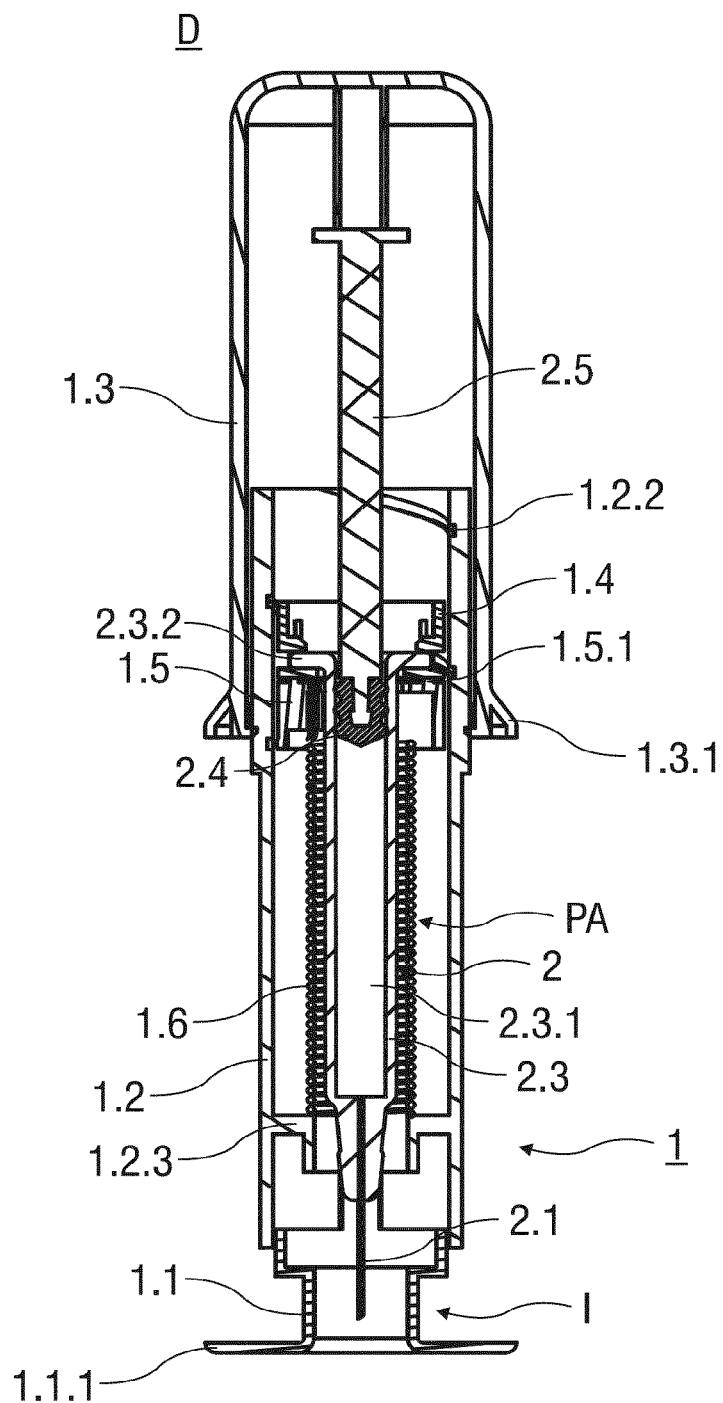
FIGS. 4A and 4B shows two different sectional views of the injection device according to the first embodiment of the invention before an injection is performed.
Figure 4B:
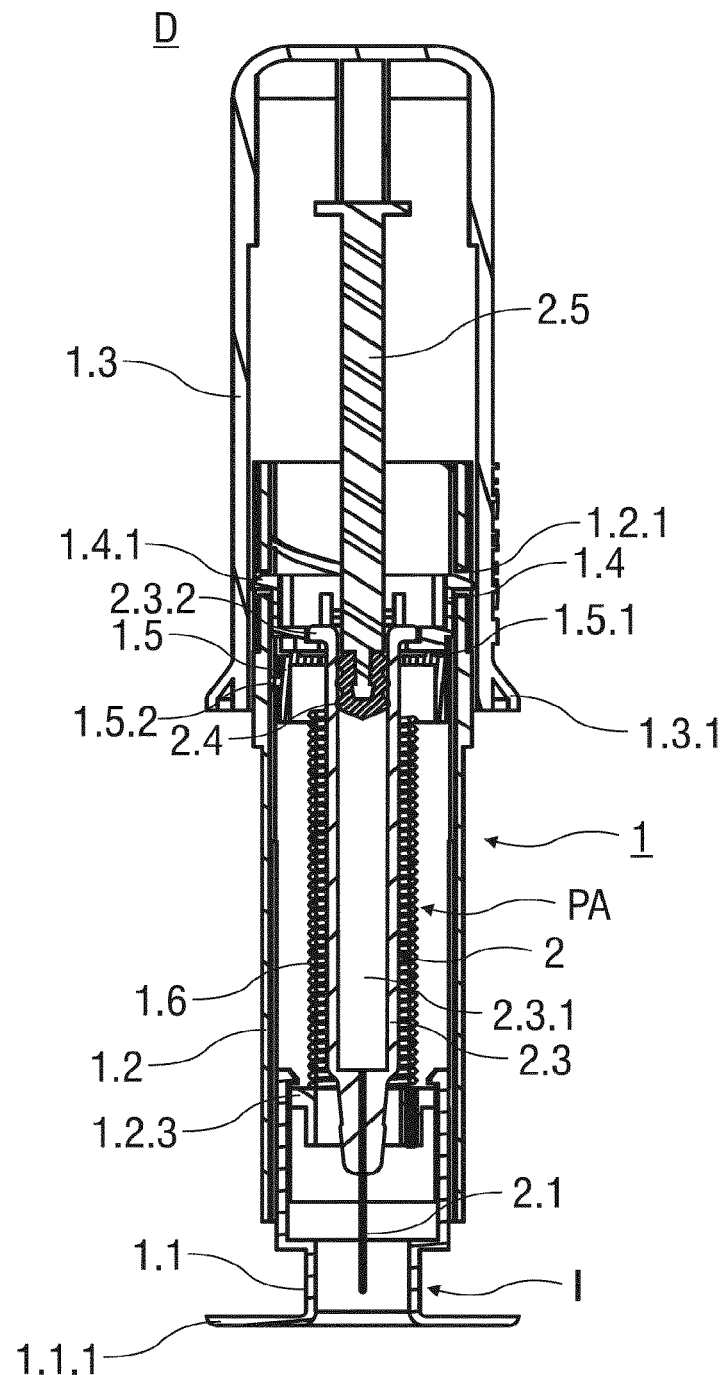

FIGS. 4A and 4B show two different sectional views of the injection device D according to the first embodiment of the invention before an injection is performed. The sectional plane shown in FIG. 4A extends perpendicularly to the one shown in FIG. 4B. The needle cap 2.2 has been pulled off to uncover the injection needle 2.1. The needle shroud 1.1 is positioned in the first position I and surrounds the injection needle 2.1 before the injection.

The injection device D comprising the safety device 1 and the pre-filled syringe 2 may be used to inject a dose of medication as follows: After removal of the needle cap 2.2, the first flange 1.1.1 of the needle shroud 1.1 is pressed against the injection site. The needle shroud 1.1 is moved from the advanced first position I towards a retracted second position II shown in FIG. 5.

Figure 5:
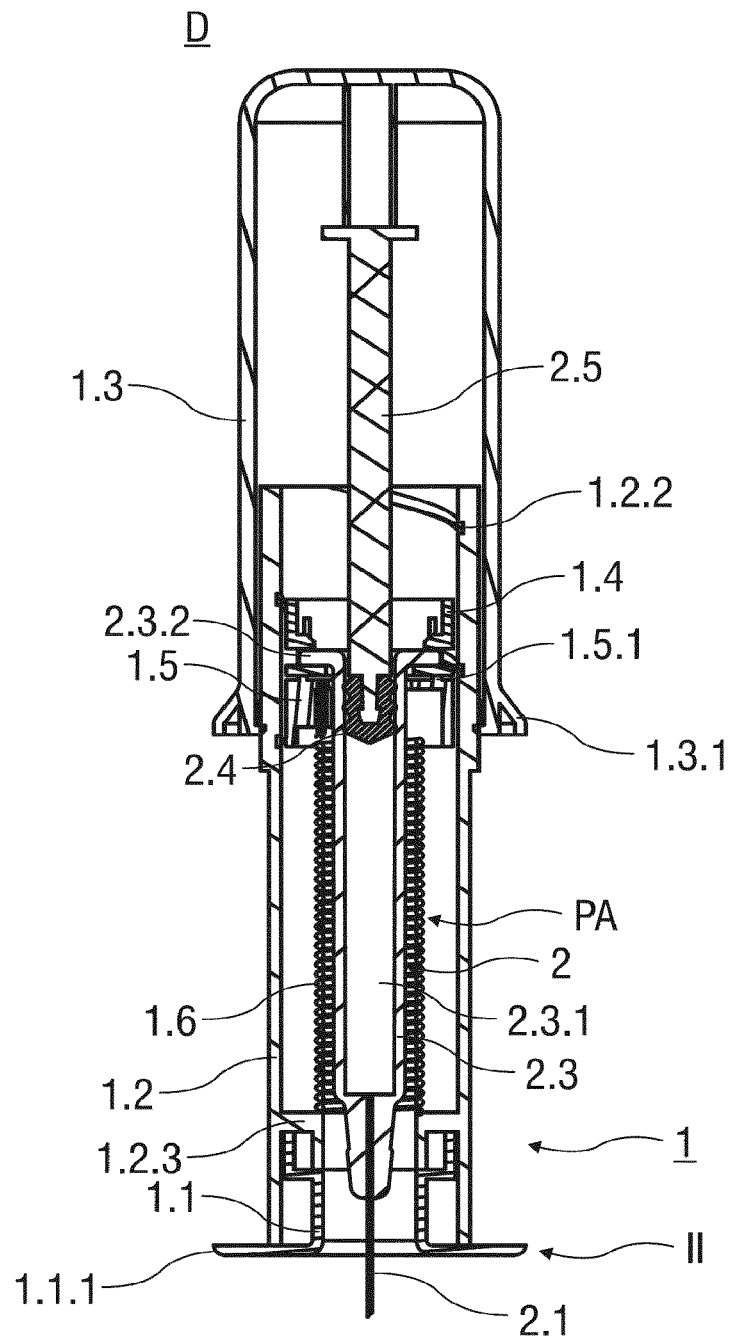
FIG. 5 shows a sectional view of the injection device according to the first embodiment of the invention comprising a needle shroud retracted in a second position.

FIG. 5 shows a sectional view of the injection device D according to the first embodiment of the invention. The needle shroud 1.1 is retracted in the second position II. The injection needle 2.1 punctures the skin of the patient receiving the injection. The outer body 1.3 is pushed distally towards the skin of the patient, whereby the plunger 2.5 is depressed into the inner cavity 2.3.1. The dose of medication contained in the inner cavity 2.3.1 is expelled through the injection needle 2.1 and disposed beneath the skin of the patient.

Figure 6:
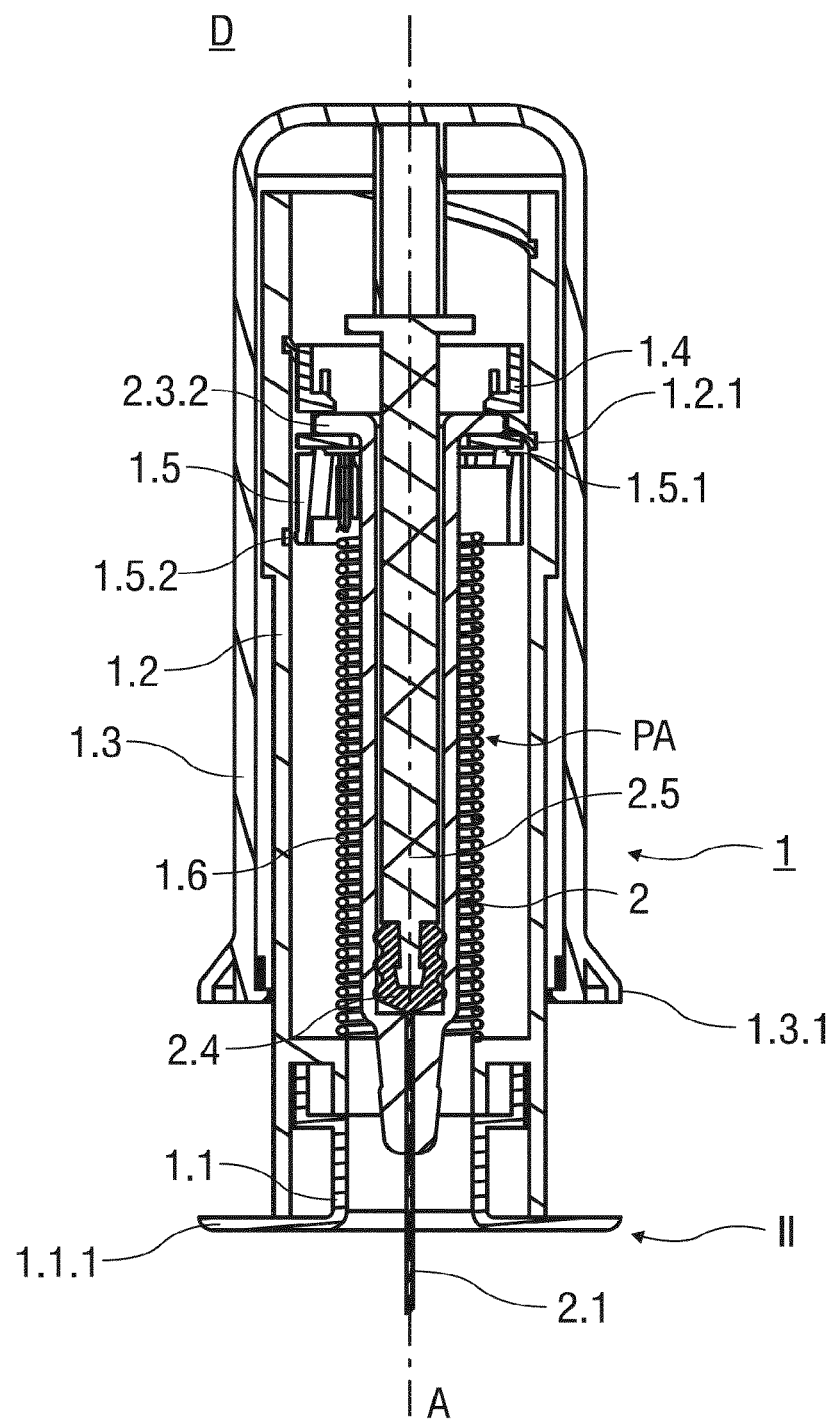
FIG. 6 shows a sectional view of the injection device according to the first embodiment of the invention at the end of an injection stroke.

The outer body 1.3 is moved distally in a single injection stroke delivering the dose of medication until the stopper 2.4 reaches a distal end of the inner cavity 2.3.1 as illustrated in FIG. 6.

FIG. 6 shows a sectional view of the injection device D according to the first embodiment of the invention at the end of an injection stroke. The plunger 2.5 is fully depressed in the inner cavity 2.3.1. The support body 1.2 is substantially received within the outer body 1.3. An inner surface of the outer body 1.3 bears against the catch 1.4.1 and deflects the catch 1.4.1 radially inwards. The catch 1.4.1 disengages the aperture 1.2.1, whereby the mounting collar 1.4 is released. The released mounting collar 1.4 is thus allowed to move proximally in a linear translatory motion.

The injection device D is removed from the injection site. The torsion spring 1.6 relaxes and exerts a torque upon the spinning collar 1.5 which in turn starts to rotate around the central axis A. As the spinning collar 1.5 is mounted to the support body 1.2 by a thread-like connection comprising the helical groove 1.2.2 accommodating the helical tongue 1.5.2, the rotating spinning collar 1.5 moves proximally within the support body 1.2. At the same time, the bearing surface 1.5.1 abuts the released mounting collar 1.4 and pushes the mounting collar 1.4 and the pre-filled syringe 2 attached thereto in the proximal direction towards a retracted position PR shown in FIG. 7.

Figure 7:
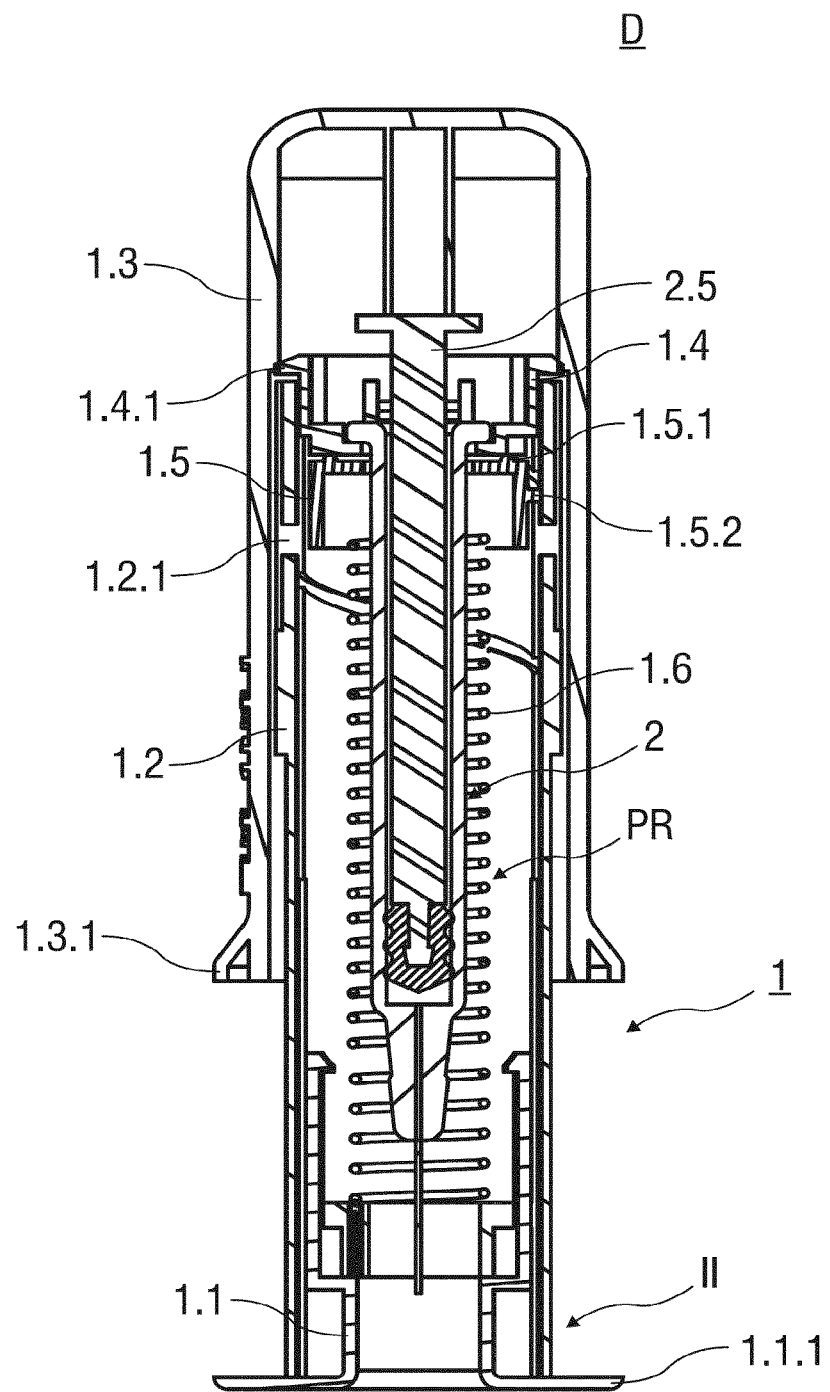
FIG. 7 shows a sectional view of the injection device according to the first embodiment of the invention with a pre-filled syringe retracted within a support body.

FIG. 7 shows a sectional view of the injection device D according to the first embodiment of the invention with the pre-filled syringe 2 located in the retracted position PR. The pre-filled syringe 2 is retracted within the support body 1.2. The needle shroud 1.1 surrounds the injection needle 2.1 to prevent accidental needle stick injuries. The catch 1.4.1 latches to a proximal end of the support body 1.2 so that a subsequent distal movement of the pre-filled syringe 2 with respect to the support body 2 is prevented. Thus, the mounting collar 1.4 and the pre-filled syringe 2 attached thereto is locked in the retracted position PR, so that a re-exposure of the injection needle 2.1 is prevented and an inadvertent contact with the used injection needle 2.1 is efficiently avoided.

Figure 8:
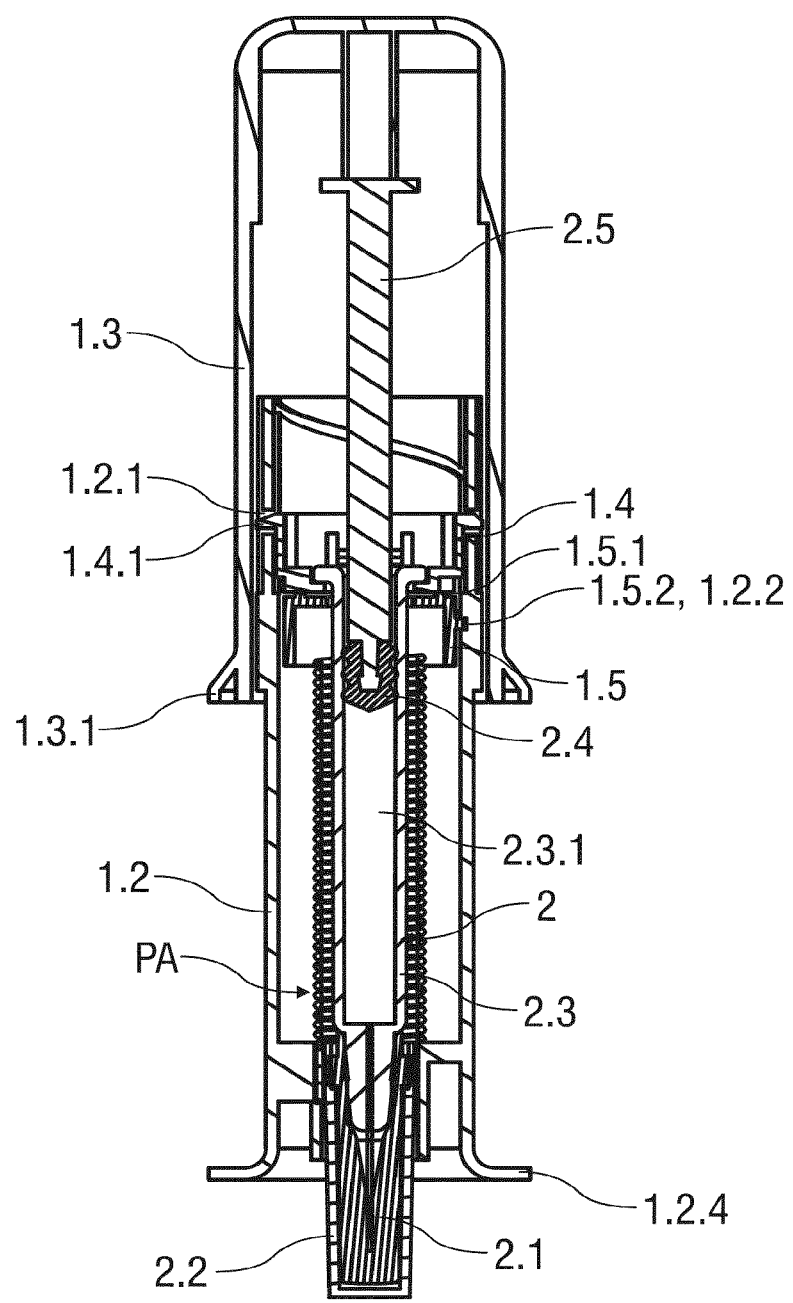
FIG. 8 shows a sectional view of an injection device according to a second embodiment in a packaged state.

FIG. 8 shows a sectional view of an injection device D according to a second embodiment in a packaged state as it would be delivered to the user. The injection device D does not comprise a needle shroud 1.1. Instead, a second flange 1.2.4, that is adapted to be pressed against the skin surface of the patient, is formed to a distal end of the support body 1.2.

After removal of the needle cap 2.2, the injection needle 2.1 is inserted into the skin of the patient. During the injection, the second flange 1.2.4 rests on the skin surface of the patient. The injection device D according to the second embodiment is designed similar to the one of the first embodiment and works essentially as described herein above. In particular, the injection is carried out as already described herein above with the exception that the needle shroud 1.1 has been omitted.

---

---

The invention claimed is:

1. A retraction mechanism for an injection device operable to administer a medicament from a pre-filled syringe, the retraction mechanism comprising:
a first member configured to be attached to the pre-filled syringe, the first member comprising a catch to lock the first member in a retracted position, the catch being deflectable to release the first member from the retracted position; and
a second member including a helical tongue extending outwardly from an outer surface of the second member, the helical tongue being configured to redirect rotational movement of the second member to translatory movement that moves the first member proximally to retract the pre-filled syringe.

2. The retraction mechanism of claim 1, wherein the first member is configured to be releasably mounted to a support body of the injection device.

3. The retraction mechanism of claim 1, wherein the catch of the first member is deflectable inwardly by an outer body of the injection device at an end of an injection stroke such that the first member is released and movable proximally relative to a support body of the injection device.

4. The retraction mechanism of claim 3, wherein the first member is configured to be attached to the pre-filled syringe such that a needle of the pre-filled syringe protrudes distally beyond the support body of the injection device in an initial position and the needle of the pre-filled syringe is surrounded by the support body in the retracted position.

5. The retraction mechanism of claim 1, wherein the catch of the first member is configured to be latched to a support body of the injection device to lock the first member in the retracted position.

6. The retraction mechanism of claim 1, wherein the first member comprises a guide member to engage a corresponding guide channel defined by a support body of the injection device to inhibit rotation of the first member relative to the support body of the injection device.

7. The retraction mechanism of claim 1, wherein:
the first member is attachable to a barrel of the pre-filled syringe, and
the second member is positionable around a barrel of the pre-filled syringe.

8. The retraction mechanism of claim 1, wherein the first member is configured to mount the pre-filled syringe within a support body of the injection device, the first member being proximally movable relative to the support body when the second member is rotated.

9. The retraction mechanism of claim 1, wherein the second member comprises a ring-shaped bearing surface that bears against a distal surface of the first member.

10. The retraction mechanism of claim 1, wherein the second member is positionable within a support body of the injection device and is rotatable relative to the support body of the injection device.

11. The retraction mechanism of claim 1, wherein the helical tongue of the second member is configured to engage a support body of the injection device such that rotational movement of the second member is redirected to translatory movement that moves the first member proximally to retract the pre-filled syringe.

12. The retraction mechanism of claim 1, wherein the second member is rotatable and translatable relative to a support body of the injection device, and the first member is configured to be rotationally fixed to and translatable relative to the support body of the injection device.

13. A retraction mechanism for an injection device operable to administer a medicament from a pre-filled syringe, the retraction mechanism comprising:
a first member configured to be attached to the pre-filled syringe, the first member rotationally fixed to and translatable relative to a support body of the injection device, the first member comprising a guide member to engage a corresponding guide channel defined by the support body of the injection device to inhibit rotation of the first member relative to the support body of the injection device; and a second member being rotatable and translatable relative to the support body of the injection device, the second member comprising a helical tongue extending outwardly from an outer surface of the second member, the helical tongue configured to redirect rotational movement of the second member to translatory movement that moves the first member proximally to retract the pre-filled syringe.

14. A retraction mechanism for an injection device operable to administer a medicament from a pre-filled syringe, the retraction mechanism comprising:

a first member configured to be attached to the pre-filled syringe; and a second member comprising a helical tongue extending outwardly from an outer surface of the second member, the helical tongue configured to redirect rotational movement of the second member to translatory movement that moves the first member proximally to retract the pre-filled syringe, wherein the first member comprises a guide member to engage a corresponding guide channel defined by the support body of the injection device to inhibit rotation of the first member relative to the support body of the injection device.

* * * * *